(12) United States Patent
McClure et al.

(10) Patent No.: US 6,353,157 B1
(45) Date of Patent: Mar. 5, 2002

(54) SOYBEAN CULTIVAR LRR969242

(76) Inventors: Donald McClure, 22146 Glen Oak Road, RR#1, Melbourne, Ontario (CA), N01 1T0; Kevin Threlkeld, 122 Golf View La., Washington, IA (US) 52353

( * ) Notice: Subject to any disclaimer, the term of this patent is extended or adjusted under 35 U.S.C. 154(b) by 0 days.

(21) Appl. No.: 09/604,588

(22) Filed: Jun. 27, 2000

(51) Int. Cl.⁷ .............................. A01H 5/00; A01H 5/10; A01H 1/02; C12N 5/04
(52) U.S. Cl. ..................... 800/312; 800/260; 435/415
(58) Field of Search ................................ 800/312, 260; 435/415

*Primary Examiner*—Elizabeth F. McElwain
(74) *Attorney, Agent, or Firm*—Bruce Vrana

(57) ABSTRACT

The invention is a novel soybean cultivar designated LRR969242 with high yield potential and tolerance to Roundup herbicide. The invention relates to seeds of the cultivar LRR969242, plants of the cultivar LRR969242, and to methods for producing a soybean plant produced by crossing the soybean LRR969242 by itself or another soybean genotype.

36 Claims, No Drawings

US 6,353,157 B1

SOYBEAN CULTIVAR LRR969242

FIELD OF THE INVENTION

The present invention relates to a new and distinctive soybean cultivar, designated LRR969242.

BACKGROUND OF THE INVENTION

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, better stems and roots, tolerance to drought and heat, and better agronomic quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars; those still deficient in a few traits may be used as parents to produce new populations for further selection.

These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of a plant breeding is to develop new, unique and superior soybean cultivars and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same soybean traits.

Each year, the plant breeder selects the germplasm to advance to the next generation. This germplasm is grown under unique and different geographical, climate and soil conditions, and further selection are then made, during and at the end of the growing season. The cultivars which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same cultivar twice by using the exact same original parents and the same selection techniques. This unpredictability results in the expenditure of large amounts of research monies to develop superior new soybean cultivars.

The development of new soybean cultivars requires the development and selection of soybean varieties, the crossing of these varieties and selection of superior hybrid crosses. The hybrid seed is produced by manual crosses between selected male-fertile parents or by using male sterility systems. These hybrids are selected for certain single gene traits such as pod color, flower color, pubescence color or herbicide resistance which indicate that the seed is truly a hybrid. Additional data on parental lines as well as the phenotype of the hybrid influence to breeder's decision whether to continue with the specific hybrid cross.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of self-pollinating crops. Two parents which possess favorable, complementary traits are crossed to produce an $F_1$. An $F_2$ population is produced by selfing one or several F's. Selection of the best individuals may begin in the $F_2$ population; then, beginning in the $F_3$, the best individuals in the families are selected. Replicated testing of families can begin the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, soybean breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in several reference books (e.g., Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer, for special advertising and marketing, altered seed and commercial production practices, and new product utilization. The testing proceeding release of a new cultivar should take into consideration research and development costs as well as technical superiority of the final cultivar. For seed-propagated cultivars, it must be feasible to produce seed easily and economically.

Soybean, *Glycine max* (L), is an important and valuable field crop. Thus, a continuing goal of plant breeders is to develop stable, high yielding soybean cultivars that are agronomically sound. The reasons for this goal are obviously to maximize the amount of grain produced on the land used and to supply food for both animals and humans. To accomplish this goal, the soybean breeder must select and develop soybean plants that have the traits that result in superior cultivars.

SUMMARY OF THE INVENTION

The invention is a novel soybean cultivar designated LRR969242 with high yield potential and tolerance to Roundup herbicide. The invention relates to seeds of the cultivar LRR969242, plants of the cultivar LRR969242, and to methods for producing a soybean plant produced by crossing the soybean LRR969242 by itself or another soybean genotype.

The invention is also directed to soybean cultivar LRR969242 further comprising one or more specific, single gene traits, for example transgenes, and which has essentially all of the morphological and physiological characteristics of cultivar LRR969242, in addition to the one or more specific, single gene traits. The invention further relates to seeds of cultivar LRR969242 further comprising one or more specific, single gene traits, plants of cultivar LRR969242 further comprising one or more specific, single gene traits, and to methods for producing a soybean plant by crossing of a soybean plant of cultivar LRR969242 further comprising one or more specific, single gene traits by itself or another soybean genotype.

DEFINITIONS

In the description and tables that follow, a number of terms are used. In order to provide a clear and consistent understanding of the specification and claims, including the scope to be given such terms, the following definitions are provided:

Seed Yield (Bushels/Acre). The yield in bushels/acre is the actual yield of the grain at harvest.

Maturity Date. Plants are considered mature when 95% of the pods have reached their mature color.

Lodging Resistance. Lodging is rated on a scale of 1 to 9. Where one is completely upright and 9 is completely prostrate.

Plant Height. Plant height is taken from the top of soil to top of node of the plant and is measured in centimeters.

Iron-Deficiency Chlorosis. Plants are scored 1 to 9 based on visual observations. A score of 1 means no stunting of the plants or yellowing of the leaves and a score of 9 indicates the plants are dead or dying caused by iron-deficiency chlorosis.

Shatter. The amount of pod dehiscence prior to harvest. Pod dehiscence involves seeds falling from the pods to the soil. This is a visual score from 1 to 9 comparing all genotypes within a given test. A score of 1 means pods have not opened and no seeds have fallen out. A score of 9 indicates 100% of the pods are opened.

DETAILED DESCRIPTION OF THE INVENTION

Parentage:A2242///S 12-49(2)//S 28-01(2)/40-3-2. A2242 is a commercial variety marketed by Asgrow Seed Co. S 12-49 and S 28-01 are commercial varieties marketed by Novartis Seeds, Inc. 40-3-2 is a line developed by Monsanto which carries their patented gene conferring tolerance to Roundup Herbicide. Seed of S 28-01 was supplied to Monsanto to make the initial cross to 40-3-2 and one backcross. This BC1F1 was planted at the NK Research Center at Waimea, Kauai, HI., in December of 1992. Plants from this F1 population were sprayed with Roundup to remove susceptible plants. Resistant plants were used as males to cross onto S 12-49. Seeds from this cross were planted at the NK Research Center at Washington, Iowa, in May of 1993 F1 plants were sprayed with Roundup, and resistant survivors were used as males in making a cross onto S 12-49. Seeds from this cross were planted at Waimea in December of 1993. F1 plants were again sprayed with Roundup and resistant plants were again used as males to cross onto A2242. Seeds from this cross were planted at Washington in May of 1994. F1 plants were sprayed with Roundup and resistant plants harvested. F2 seeds from this cross were planted at Waimea in December of 1994 and sprayed with Roundup. The F2 and F3 populations were grown at the Novartis Seeds, Inc. Research Farm at Kekaha, Kauai, HI., in the winter of 1994-95 and the F4 generation was grown at Washington Iowa in the summer of 1995 and sprayed with Roundup. In September 85 single plants were harvested and threshed individually. The progeny were tested in a preliminary trial at Novartis Seeds Inc., Arva, Ontario in 1996. One of these, designated LRR969242, was selected for advancement to a second year retest in 1997 and was tested in advanced trials in the Onatrio and the Midwest U.S. in 1998-99.

LRR969242 was also tested in the greenhouse at the Novartis Seeds, Inc. Research Center at Bay, AR for resistance to *Phytophthora sojae* in 1999 and 2000 and found to have the Rps1-k gene for resistance, C. K. Moots, C. D. Nickel, L. E. Gray, and S. M. Lim, Reaction of Soybean Cultivars to 14 Races of Phytophthora megasperma f.s., glycina. Plant Disease 67:764-767.

A soybean cultivar needs to be highly homogeneous, homozygous and reproducible to be useful as a commercial cultivar. There are many analytical methods available to determine the homozygotic and phenotypic stability of these varieties.

The oldest and most traditional method of analysis is the observation of phenotypic traits. The data is usually collected in field experiments over the life of the soybean plants to be examined. Phenotypic characteristics most often observed are for traits associated with seed yield, lodging resistance, disease resistance, emergence, maturity, plant height, shattering, flower color, pubescence color, pod color and hilum color.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites.

The cultivar of the invention has shown uniformity and stability for all traits, as described in the following variety description information. It has been self-pollinated a sufficient number of generations, with careful attention to uniformity of plant type to ensure homozygosity and phenotypic stability. The line has been increased with continued observation for uniformity. No variant traits have been observed or are expected in LRR969242. Soybean cultivar LRR969242, being substantially homozygous, can be reproduced by planting seeds of the line, growing the resulting soybean plants under self-pollinating or sib-pollinating conditions, and harvesting the resulting seed, using techniques familiar to the agricultural arts.

Publications useful as references in interpreting the data presented below include: Caldwell, B. E. ed. 1973. "Soybeans: Improvement, Production, and Uses" Amer. Soc. Agron. Monograph No. 16; Buttery, B. R., and R. I. Buzzell 1968. "Peroxidase Activity in Seed of Soybean Varieties" Crop Sci. 8: 722–725; Hymowitz, T. 1973. "Electrophoretic analysis of SBTI-A2 in the USDA Soybean Gemiplasm Collection" Crop Sci., 13: 420–421; Payne R. C., and L. F. Morris, 1976. "Differentiation of Soybean Varieties by Seedling Pigmentation Patterns" J. Seed. Technol. 1: 1–19. The disclosures of which are each incorporated by reference in their entirety.

Soybean cultivar LRR969242 has the following morphologic and other characteristics:

| Plant Type: | Intermediate | Seed Cotyledon Color: | Yellow |
|---|---|---|---|
| Hypocotyl Length: | Long | Seed Peroxidase Activity: | Low |
| Leaf Shape: | Ovate | Phytophthora Res. Gene | Rpsl-k |
| Stem Termination: | Indeterminate | Maturity Group | 0 |
| Pubescence Color: | Tawny | Relative Maturity | 0.8 |
| Flower Color: | White | Ave. Seeds per Pound | 2800 |
| Pod Color: | Tan | | |
| Seed Hilum Color: | Gray | | |
| Hypocotyl Color: | Green with bronze band below cotyledons | | |
| Leaf Color: | Medium Green | | |
| Seed Coat Color: | Yellow | | |

The invention also encompasses plants of cultivar LRR969242 and parts thereof further comprising one or more specific, single gene transferred traits. Such traits are introgressed into cultivar LRR969242 from another soybean cultivar or are directly transformed into cultivar LRR969242. Preferably, one or more new traits are transferred to cultivar LRR969242, or, alternatively, one or more traits of cultivar LRR969242 are altered or substituted. The introgression of the trait(s) into cultivar LRR969242 is for example achieved by recurrent selection breeding, for example by backcrossing. In this case, cultivar LRR969242 (the recurrent parent) is first crossed to a donor inbred (the non-recurrent parent) that carries the appropriate gene(s) for the trait(s) in question. The progeny of this cross is then mated back to the recurrent parent followed by selection in the resultant progeny for the desired trait(s) to be transferred from the non-recurrent parent. After three, preferably four, more preferably five or more generations of backcrosses with the recurrent parent with selection for the desired trait(s), the progeny will be heterozygous for loci controlling the trait(s) being transferred, but will be like the recurrent parent for most or almost all other genes (see, for example, Poehlman & Sleper (1995) Breeding Field Crops, 4th Ed., 172–175; Fehr (1987) Principles of Cultivar Development, Vol. 1: Theory and Technique, 360376, incorporated herein by reference).

The laboratory-based techniques described above, in particular RFLP and SSR, can be used in such backcrosses to identify the progenies having the highest degree of genetic identity with the recurrent parent. This permits one to accelerate the production of soybean cultivars having at least 90%, preferably at least 95%, more preferably at least 99% genetic identity with the recurrent parent, yet more preferably genetically identical to the recurrent parent, and further comprising the trait(s) introgressed from the donor patent. Such determination of genetic identity can be based on molecular markers used in the laboratory-based techniques described above.

The last backcross generation is then selfed to give pure breeding progeny for the gene(s) being transferred. The resulting plants have essentially all of the morphological and physiological characteristics of cultivar LRR969242, in addition to the single gene trait(s) transferred to the inbred. The exact backcrossing protocol will depend on the trait being altered to determine an appropriate testing protocol. Although backcrossing methods are simplified when the trait being transferred is a dominant allele, a recessive allele may also be transferred. In this instance it may be necessary to introduce a test of the progeny to determine if the desired trait has been successfully transferred.

The cultivar of the invention can also be used for transformation where exogenous genes are introduced and expressed by the cultivar of the invention. Genetic variants created either through traditional breeding methods using cultivar LRR969242 or through transformation of cultivar LRR969242 by any of a number of protocols known to those of skill in the art are intended to be within the scope of this invention (see e.g. Trick et al. (1997) Recent advances in soybean transformation, in Plant Tissue Culture and Biotechnology, 3:9–26, incorporated herein by reference).

Production of a genetically modified plant tissue by transformation combines teachings of the present disclosure with a variety of techniques and expedients known in the art. In most instances alternate expedients exist for each stage of the overall process. The choice of expedients depends on the variables such as the plasmid vector system chosen for the cloning and introduction of the desired recombinant DNA molecule, as well as the particular structural gene, promoter elements and upstream elements used. Persons skilled in the art are able to select and use appropriate alternatives to achieve functionality. Culture conditions for expressing desired structural genes and cultured cells are known in the art. Also as known in the art, soybeans are transformable and regenerable such that whole plants containing and expressing desired genes under regulatory control may be obtained. General descriptions of plant expression vectors and reporter genes and transformation protocols can be found in Gruber, et al., "Vectors for Plant Transformation, in Methods in Plant Molecular Biology & Biotechnology" in Glich et al., (Eds. pp. 89–119, CRC Press, 1993). Moreover GUS expression vectors and GUS gene cassettes are available from Clone Tech Laboratories, Inc., Palo Alto, Calif. while luciferase expression vectors and luciferase gene cassettes are available from Pro Mega Corp. Madison, Wis.). General methods of culturing plant tissues are provided for example by Maki et al. "Procedures for Introducing Foreign DNA into Plants" in Methods in Plant Molecular Biology & Biotechnology, Glich et al. (Eds. pp. 67–88 CRC Press, 1993); and by Phillips et al. "Cell-Tissue Culture and In-Vitro Manipulation" in Corn & Corn Improvement, 3rd Edition Sprague et al. (Eds. pp. 345–387) American Society of Agronomy Inc. et al. 1988.

Methods of introducing desired recombinant DNA molecule into plant tissue include the direct infection or co-cultivation of plant cells with Agrobacterium tumefaciens, Horsch et al., Science, 227:1229 (1985). Descriptions of Agrobacterium vector systems and methods for Agrobacterium-mediated gene transfer provided by Gruber, et al. supra. Other useful methods include but are not limited to expression vectors introduced into plant tissues using a direct gene transfer method such as microprojectile-mediated delivery, DNA injection, electroporation and the like. More preferably expression vectors are introduced into plant tissues using the biolistic microprojectile delivery or Agrobacterium-medicated transformation. Transformed plants obtained via protoplast transformation are also intended to be within the scope of this invention.

Many traits have been identified that are not regularly selected for in the development of a new cultivar but that can be improved e.g. by backcrossing techniques or by genetic transformation. Examples of traits transferred to cultivar LRR969242 include, but are not limited to, herbicide tolerance, resistance for bacterial, fungal, or viral disease, nematode resistance, insect resistance, enhanced nutritional quality, such as oil, starch and protein content or quality, improved performance in an industrial process, altered reproductive capability, such as male sterility or male fertility, yield stability and yield enhancement. Other traits transferred to cultivar LRR969242 are for the production of commercially valuable enzymes or metabolites in plants of cultivar LRR969242.

Traits transferred to soybean cultivar LRR969242 are naturally occurring soybean traits or are transgenic. Transgenes are directly introduced into cultivar LRR969242 using genetic engineering and transformation techniques well known in the art or described above, or are originally introduced into a donor, non-recurrent parent using genetic engineering and transformation techniques and are then introgressed into cultivar LRR969242, for example by backcrossing. A transgene typically comprises a nucleotide sequence whose expression is responsible or contributes to the trait, under the control of a promoter capable of directing the expression of the nucleotide sequence at the desired time in the desired tissue or part of the plant. Constitutive, tissue-specific or inducible promoters preferably are used. The transgene may also comprise other regulatory elements such as for example translation enhancers or termination signals. In a preferred embodiment, the nucleotide sequence is the coding sequence of a gene and is transcribed and translated into a protein. In another preferred embodiment, the nucleotide sequence encodes an antisense RNA or a sense RNA that is not translated or only partially translated.

Where more than one trait are introgressed into cultivar LRR969242, it is preferred that the specific genes are all located at the same genomic locus in the donor, non-recurrent parent, preferably, in the case of transgenes, as part of a single DNA construct integrated into the donor's genome. Alternatively, if the genes are located at different genomic loci in the donor, non-recurrent parent, backcrossing allows to recover all of the morphological and physiological characteristics of cultivar LRR969242 in addition to the multiple genes in the resulting soybean cultivar.

The genes responsible for a specific, single gene trait are generally inherited through the nucleus. Known exceptions are, e.g. the genes for male sterility, some of which are inherited cytoplasmically, but still act as single gene traits. In a preferred embodiment, a transgene to be introgressed into cultivar LRR969242 is integrated into the nuclear genome of the donor, non-recurrent parent or the transgene is directly transformed into the nuclear genome of cultivar LRR969242. In another preferred embodiment, a transgene to be introgressed into cultivar LRR969242 is integrated into the plastid genome of the donor, non-recurrent parent or the transgene is directly transformed into the plastid genome of cultivar LRR969242. In a preferred embodiment, a plastid transgene comprises one gene transcribed from a single promoter or two or more genes transcribed from a single promoter.

A trait transferred to cultivar LRR969242 is for example resistance to brown stem rot (U.S. Pat. No. 5,689,035) or resistance to cyst nematodes (U.S. Pat. No. 5,491,081), both incorporated herein by reference. In a preferred embodiment, a transgene whose expression results or contributes to a desired trait to be transferred to cultivar LRR969242 comprises a gene encoding an insecticidal protein, such as, for example, a crystal protein of *Bacillus thuringiensis* or a vegetative insecticidal protein from *Bacillus cereus*, such as VIP3 (see for example Estruch et al. Nat Biotechnol (1997) 15:137-41, incorporated herein by reference). In another preferred embodiment, a transgene introgressed into cultivar LRR969242 comprises a herbicide tolerance gene whose expression renders plants of cultivar LRR969242 tolerant to the herbicide. For example, expression of an altered acetohydroxyacid synthase (AHAS) enzyme confers upon plants tolerance to various imidazolinone or sulfonamide herbicides (U.S. Pat. No. 4,761,373, incorporated herein by reference). In another preferred embodiment, a non-transgenic trait conferring tolerance to imidazolinones or sulfonylurea herbicides is introgressed into cultivar LRR969242. Expression of a mutant acetolactate synthase (ALS) that render the plants resistant to inhibition by sulfonylurea herbicides (U.S. Pat. No. 5,013,659), incorporated herein by reference. In another preferred embodiment, U.S. Pat. No. 4,975,374, incorporated herein by reference, relates to plant cells and plants containing a gene encoding a mutant glutamine synthetase (GS) resistant to inhibition by herbicides that are known to inhibit GS, e.g. phosphinothricin and methionine sulfoxirine. Also, expression of a *Streptomyces bar* gene encoding a phosphinothricin acetyl transferase in maize plants results in tolerance to the herbicide phosphinothricin or glufosinate (U.S. Pat. No. 5,489,520, incorporated herein by reference). U.S. Pat. No. 5,162,602, incorporated herein by reference, discloses plants tolerant to inhibition by cyclohexanedione and aryloxyphenoxypropanoic acid herbicides. The tolerance is conferred by an altered acetyl coenzyme A carboxylase(ACCase). U.S. Pat. No. 5,554,798, incorporated herein by reference, discloses transgenic glyphosate tolerant maize plants, which tolerance is conferred by an altered 5-enolpyruvyl-3-phosphoshikimate (EPSP) synthase gene. In another preferred embodiment, tolerance to a protoporphyrinogen oxidase inhibitor is achieved by expression of a tolerant protoporphyrinogen oxidase enzyme in plants (U.S. Pat. No. 5,767,373, incorporated herein by reference). In a preferred embodiment, a transgene introgressed into cultivar LRR969242 comprises a gene conferring tolerance to a herbicide and at least another nucleotide sequence for another trait, such as for example, insect resistance or tolerance to another herbicide.

Specific transgenic events introgressed into cultivar LRR969242 are for example introgressed from events G94-1, G94-19 or G-168 with altered oil profile, from phosphinothricin tolerant events W62, W98, A2704-12, A2704-21 or A5547-35 or from glyphosate tolerant event 40-3-2.

Direct selection may be applied where the trait acts as a dominant trait. An example of a dominant trait is herbicide tolerance. For this selection process, the progeny of the initial cross are sprayed with the herbicide prior to the backcrossing. The spraying eliminates any plant which do not have the desired herbicide tolerance characteristic, and only those plants which have the herbicide tolerance gene are used in the subsequent backcross. This process is then repeated for the additional backcross generations.

This invention is also directed to methods for producing a soybean plant by crossing a first parent soybean plant with a second parent soybean plant, wherein the first or second soybean plant is the soybean plant from the line LRR969242. Further, both first and second parent soybean plants may be from the cultivar LRR969242. Therefore, any methods using the cultivar LRR9692426 are part of this invention; selfing, backcrosses, hybrid breeding, and crosses to populations. Any plants produced using cultivar LRR969242 or cultivar LRR969242 tier comprising one or more specific, single gene traits as a parent are within the scope of this invention. For example, the soybean cultivar LRR969242 or cultivar LRR969242 further comprising one or more specific, single gene traits are used in crosses with other, different, soybean plants to produce first generation (F1) soybean hybrid seeds and plants with superior characteristics. For example, a method to produce a hybrid soybean seed comprises the steps of planting, preferably in pollinating proximity, seeds of soybean cultivar LRR969242 or seeds of soybean cultivar LRR969242 further comprising one or more specific, single gene traits and another soybean cultivar, cultivating the soybean plants resulting from said seeds until said plants bear flowers, emasculating the plants of either one or the other soybean cultivar, inducing cross pollination to occur between said soybean cultivars and harvesting seeds produced on said emasculated plants of the cultivar line.

As used herein, the term "plant" includes plant cells, plant protoplasts, plant cells of tissue culture from which soybean plants can be regenerated, plant calli, plant clumps, and plant cells that are intact in plants or parts of plants, such as pollen, flowers, seeds, pods, leaves, stems, and the like. Thus, another aspect of this invention is to provide for cells that upon growth and differentiation produce the cultivar LRR969242.

Further reproduction of the cultivar can occur by tissue culture and regeneration. Tissue culture of various tissues of soybeans and regeneration of plants therefrom is well known and widely published. For example, reference may be had to Komatsuda, T. et al., "Genotype X Sucrose Interactions for Somatic Embryogenesis in Soybean," Crop Sci. 31:333–337 (1991); Stephens, P. A. et al., "Agronomic Evaluation of Tissue-Culture-Derived Soybean Plants," Theor. Appl. Genet. (1991) 82:633–635; Komatsuda, T. et al., "Maturation and Germination of Somatic Embryos as Affected by Sucrose and Plant Growth Regulators in Soybeans *Glycine gracilis* Skvortz and *Glycine max* (L.) Merr.," Plant Cell, Tissue and Organ Culture, 28:103–113 (1992); Dhir, S. et al., "Regeneration of Fertile Plants from Protoplasts of Soybean (*Glycine max* L. Merr.): Genotypic Differences in Culture Response," Plant Cell Reports (1992) 11:285–289; Pandey, P. et al., "Plant Regeneration from Leaf and Hypocotyl Explants of *Glycine wightii* (W. and A.) VERDC. var longicauda," Japan J. Breed. 42:1–5 (1992); and Shetty, K., et al., "Stimulation of In Vitro Shoot Organogenesis in *Glycine max* Merrill.) by Allantoin and Amides," Plant Science 81: (1992) 245–251; as well as U.S. Pat. No. 5,024,944, issued Jun. 18, 1991 to Collins et al. and U.S. Pat. No. 5,008,200, issued Apr. 16, 1991 to Ranch et al., the disclosures of which are hereby incorporated herein in their entirety by reference. Thus, another aspect of this invention is to provide cells which upon growth and differentiation produce soybean plants having the physiological and morphological characteristics of cultivar LRR969242.

The seed of soybean cultivar LRR969242 or soybean cultivar LRR969242 further comprising one or more specific, single gene traits, the plant produced from the seed, the hybrid soybean plant produced from the crossing of the variety with any other soybean plant, hybrid seed, and various parts of the hybrid soybean plant can be utilized for human food, livestock feed, and as a raw material in industry.

Soybean is the world's leading source of vegetable oil and protein meal. The oil extracted from soybeans is used for cooking oil, margarine, and salad dressings. Soybean oil is composed of saturated, monounsaturated and polyunsaturated fatty acids. It has a typical composition of 11% palmitic, 4% stearic, 25% oleic, 50% linoleic and 9% linolenic fatty acid content ("Economic Implications of Modified Soybean Traits Summary Report", Iowa Soybean Promotion Board & American Soybean Association Special Report 92S, May 1990. Changes in fatty acid composition for improved oxidative stability and nutrition are constantly sought after. Industrial uses of soybean oil which is subjected to further processing include ingredients for paints, plastics, fibers, detergents, cosmetics, and lubricants. Soybean oil may be split, inter-esterified, sulfurized, epoxidized, polymerized, ethoxylated, or cleaved. Designing and producing soybean oil derivatives with improved functionality, oliochemistry, is a rapidly growing field. The typical mixture of triglycerides is usually split and separated into pure fatty acids, which are then combined with petroleum-derived alcohols or acids, nitrogen, sulfonates, chlorine, or with fatty alcohols derived from fats and oils.

Soybean is also used as a food source for both animals and humans. Soybean is widely used as a source of protein for animal feeds for poultry, swine and cattle. During processing of whole soybeans, the fibrous hull is removed and the oil is extracted. The remaining soybean meal is a combination of carbohydrates and approximately 50% protein. For human consumption soybean meal is made into soybean flour which is processed to protein concentrates used for meat extenders or specialty pet foods. Production of edible protein ingredients from soybean offers a healthy, less expensive replacement for animal protein in meats as well as dairy-type products.

TABLE

LRR969242 was tested in Novartis Seeds, Inc. Advanced Yield Trials in 1999. Data were collected for yield (bushels per acre), maturity date (95% mature pod color), lodging score (1 = completely upright, 9 = completely prostrate), plant height (cm.), iron chlorosis score (1 = highly resistant, 9 = highly susceptible), and pod shatter score (1 = no shatter, 9 = all pods shattered). Data are summarized in the following table.

| Variety | Yield Ave. 18 | Maturity Ave.13 | Lodging Ave.11 | Height Ave.3 | Iron Chlorosis Ave. 2 | Shatter Ave. 3 |
|---|---|---|---|---|---|---|
| LRR969242 | 47.2 | 9–13 | 2.1 | 84 | 4.5 | 6.1 |
| S14-M7 | 46.6 | 9–20 | 3.2 | 95 | 3.3 | 3.5 |
| 2801R | 44.5 | 9–17 | 3.9 | 104 | 4.0 | 6.9 |
| 90B72 | 44.0 | 9–12 | 4.1 | 94 | 4.3 | 5.6 |
| 91B02 | 43.8 | 9–14 | 2.3 | 85 | 6.5 | 7.9 |
| 2701R | 37.4 | 9–11 | 3.0 | 85 | 6.0 | 5.8 |
| Mean | 48.4 | 9–15 | 2.9 | 89 | 4.3 | 4.8 |
| LSD .05 | 2.3 | 1 | 0.6 | 6 | 2.2 | 1.2 |

DEPOSIT INFORMATION

Applicants have made a deposit of at least 2500 seeds of the cultivar of the present invention with the American Type Culture Collection (ATCC), Manassas, Va., 20110-2209 U.S.A., ATCC Accession No: PTA-3636. This deposit of cultivar LRR969242 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicants have satisfied all the requirements of 37 C.F.R. §§1.801–1.809, including providing an indication of the viability of the sample. Applicants impose no restrictions on the availability of the deposited material from the ATCC; however, Applicants have no authority to waive any restrictions imposed by law on the transfer of biological material or its transportation in commerce. Applicants do not waive any infringement of its rights granted under this patent or under the Plant Variety Protection Act (7 USC 2321 et seq.).

The foregoing invention has been described in detail by way of illustration and example for purposes of clarity and understanding. However, it will be obvious that certain changes and modifications such as single gene modifications and mutations, somaclonal variants, variant individuals selected from large populations of the plants of the instant inbred and the like may be practiced within the scope of the invention, as limited only by the scope of the appended claims.

What is claimed is:

1. Seed of soybean cultivar LRR969242 having been deposited under ATCC Accession No: PTA-3636.

2. A soybean plant, or parts thereof, of cultivar LRR969242, seed of said cultivar having been deposited under ATCC Accession No: PTA-3636.

3. Pollen of the plant of claim 2.

4. An ovule of the plant of claim 2.

5. A soybean plant, or parts thereof, having all the physiological and morphological characteristics of a plant according to claim 2.

6. A soybean plant, or parts thereof, having all the physiological and morphological characteristics of a plant according to claim 2, and further comprising a single gene transferred trait.

7. A soybean plant, or parts thereof, according to claim 6, wherein the plant or parts thereof have been transformed so that its genetic material contains a transgene operably linked to one or more regulatory elements.

8. A soybean plant according to claim 7, wherein said transgene comprises a gene conferring upon said soybean plant tolerance to a herbicide.

9. A soybean plant according to claim 8, wherein said herbicide is glyphosate, glufosinate, a sulfonylurea or an imidazolinone herbicide, or a protoporphyrinogen oxidase inhibitor.

10. A soybean plant according to claim 7, wherein said transgene comprises a gene conferring upon said soybean plant insect resistance, disease resistance, nematode resistance or virus resistance.

11. A soybean plant according to claim 10, wherein said gene conferring upon said soybean plant insect resistance comprises a VIP3 gene.

12. A tissue culture of regenerable cells of a soybean plant according to claim 2, wherein the tissue regenerates plants capable of expressing all the morphological and physiological characteristics of a plant according to claim 2.

13. A soybean plant regenerated from the tissue culture of claim 12, capable of expressing all the morphological and physiological characteristics of cultivar LRR969242, seed of said cultivar having been deposited under ATCC Accession No: PTA-3636.

14. A method for producing a soybean seed comprising crossing a first parent soybean plant with a second parent soybean plant and harvesting the resultant first generation soybean seed, wherein said first or second parent soybean plant is a soybean plant according to claim 2 or a soybean plant having all the physiological and morphological characteristics of a plant according to claim 2.

15. The method according to claim 14, wherein said first parent soybean plant is different from said second parent soybean plant, wherein said resultant seed is a first generation (F1) hybrid soybean seed.

16. The method according to claim 14, wherein said soybean plant of cultivar LRR969242, seed of said cultivar having been deposited under ATCC Accession No: PTA-3636, or said soybean plant having all the physiological and morphological characteristics of a plant of cultivar LRR969242 is the female parent.

17. The method according to claim 14, wherein said soybean plant of cultivar LRR969242, seed of said cultivar having been deposited under ATCC Accession No: PTA-3636, or said soybean plant having all the physiological and morphological characteristics of a plant of cultivar LRR969242 is the male parent.

18. An F1 hybrid soybean seed produced by the method of claim 15.

19. An F1 hybrid soybean plant, or parts thereof, grown from the seed of claim 18.

20. A method for producing soybean seed comprising crossing a first parent soybean plant with a second parent soybean plant and harvesting the resultant first generation soybean seed, wherein said first or second parent soybean plant is a soybean plant according to claim 6.

21. The method according to claim 20, wherein said first parent soybean plant is different from said second parent soybean plant, wherein said resultant seed is a first generation F1) hybrid soybean seed.

22. The method according to claim 21, wherein said soybean plant of cultivar LRR969242, seed of said cultivar having been deposited under ATCC Accession No: PTA-3636, is the female parent.

23. The method according to claim 21, wherein said soybean plant of cultivar LRR969242, seed of said cultivar having been deposited under ATCC Accession No: PTA-3636, is the female parent.

24. An F1 hybrid soybean seed produced by the method of claim 21.

25. An F1 hybrid soybean plant, or parts thereof, grown from the seed of claim 24.

26. A method for producing soybean seed comprising crossing a first parent soybean plant with a second parent soybean plant and harvesting the resultant first generation soybean seed, wherein said first or second parent soybean plant is the inbred soybean plant of claim 6.

27. The method according to claim 26, wherein said first parent soybean plant is different from said second parent soybean plant, wherein said resultant seed is a first generation (F1) hybrid soybean seed.

28. A method to produce a hybrid soybean seed comprising the steps of:
   a) planting in pollinating proximity seeds of soybean cultivar LRR969242, seed of said cultivar having been deposited under ATCC Accession No: PTA-3636, or seeds of a soybean plant having all the physiological and morphological characteristics of a plant of cultivar LRR969242, or seeds of a soybean plant having all the physiological and morphological characteristics of a plant of cultivar LRR969242 and further comprising one or more single gene transferred traits, and seeds of another soybean cultivar;
   b) cultivating soybean plants resulting from said seeds until said plants bear flowers;
   c) emasculating the male flower parts of the plants of either one or the other soybean cultivar;
   d) inducing cross pollination to occur between said soybean cultivars; and
   e) harvesting seeds produced on said emasculated plants of the cultivar.

29. The method according to claim 28, wherein said one parent has all the physiological and morphological characteristics of inbred soybean line LRR969242, seed of said line having been deposited under ATCC Accession No: PTA-3636, and further comprises a single gene transferred trait.

30. The method according to claim 28 wherein said step of identifying said inbred plant comprises: identifying plants with decreased vigor compared to hybrid plants grown from said hybrid seed.

31. A method comprising introgressing a single gene trait into inbred soybean line LRR969242, seed of said line having been deposited under ATCC Accession No: PTA-3636, using one or more markers for marker assisted selection among soybean lines to be used in a soybean breeding program, the markers being associated with said single gene trait, wherein the resulting soybean line has essentially all the physiological and morphological characteristics of a plant of inbred line LRR969242 and further comprises said single gene trait.

32. A first generation ($F_1$) hybrid soybean plant produced by growing said hybrid soybean seed of claim 28.

33. A method for developing a soybean plant in a soybean breeding program using plant breeding techniques, which include employing a soybean plant, or its parts thereof, as a source of breeding material, comprising: using the soybean plant, or its parts thereof, of claim 2 as a source of breeding material.

34. The method of claim 33, wherein plant breeding techniques are selected from the group of: recurrent selection, backcrossing, pedigree breeding, restriction fragment length polymorphism enhanced selection, genetic marker enhanced selection, and transformation.

35. A soybean plant according to claim 6, wherein said single gene transferred trait comprise a gene which is first introduced by transgenic methods into a soybean line different from said inbred soybean line LRR969242 and then introgressed into said inbred soybean line LRR969242.

36. Seeds of a plant according to claim 6.

* * * * *